US005906723A

United States Patent [19]
Mathies et al.

[11] Patent Number: 5,906,723
[45] Date of Patent: May 25, 1999

[54] ELECTROCHEMICAL DETECTOR INTEGRATED ON MICROFABRICATED CAPILLARY ELECTROPHORESIS CHIPS

[75] Inventors: Richard A. Mathies, Moraga; Alexander N. Glazer, Orinda; Kaiqin Lao, San Francisco; Adam T. Woolley, Albany, all of Calif.

[73] Assignee: The Regents of the University of California, Berkeley, Calif.

[21] Appl. No.: 08/703,394

[22] Filed: Aug. 26, 1996

[51] Int. Cl.$^6$ .................................................. G01N 27/26
[52] U.S. Cl. ............................................ 204/603; 204/601
[58] Field of Search .................... 204/451, 452, 204/601, 603

[56] References Cited

U.S. PATENT DOCUMENTS

| | | | |
|---|---|---|---|
| 4,891,120 | 1/1990 | Sethi et al. | 204/600 |
| 5,071,531 | 12/1991 | Soane | 204/182.8 |
| 5,126,022 | 6/1992 | Soane | 204/180.1 |
| 5,132,012 | 7/1992 | Miura et al. | 210/198.2 |
| 5,141,868 | 8/1992 | Shanks et al. | 435/287.9 |
| 5,194,133 | 3/1993 | Clark et al. | 204/608 |

FOREIGN PATENT DOCUMENTS

| | | |
|---|---|---|
| 4314755 | 11/1994 | Germany . |
| WO95/10040 | 4/1995 | WIPO . |

OTHER PUBLICATIONS

Jonathan M. Slater, et al. (On–chip Microband Array Electrochenical Detector for use in Capillary Electrophoresis, Analyst, Nov. 1994, vol. 119, pp. 2303–2307).

Gavin, Peter F., et al.; "Continuous Separations with Microfabricated Electrophoresis—Electrochemical Array Detection", J. Am. Chem. Soc. (1996), vol. 118, pp. 8932–8936.

Adam T. Woolley, et al., Ultra–high–speed DNA fragment separations using microfabricated capillary array electrophoresis chips, Proc. Natl. Acad. Sci., vol. 91, pp. 11348–11352, Nov. 1994, Biophysics.

Mark K. Shigenaga, et al., In Vivo Oxidative DNA Damage . . . , Methods in Enzymology, vol. 186, pp. 521–530. 1990 month unavailable.

Dan Wu, et al., Electrophoretically mediated mico–assay of alkaline phosphatase using electrochemical and spectrophotometric detection in capillary electrophoresis, Journal of Chromatography B, 656 (1994) month unavailable pp. 357–363.

Dean H. Johnston, et al., Electrochemical Measurement of the Solvent Accessibility of Nucleobases Using Electron Transfer between DNA and Metal Complexes, J. Am. Chem. Soc. 1995 month unavailable, 117, pp. 8933–8938.

Teresa M. Olefirowicz, et al., Capillary Electrophoresis in 2 and 5 $\mu$m Diameter Capillaries: Application to Cytoplasmic Analysis, Anal. Chem. month unavailable 1990, 62, pp. 1872–1876.

Karin Pihel, et al., Electrochemical Detection of Histamine and 5–Hydroxytryptamine at Isolated Mast Cells, Anal. Chem. month unavailable 1995, 67, pp. 4514–4521.

Fu–Ren F. Fan, et al. Electrochemical Detection of Single Molecules, Science, vol. 267, Feb. 10, 1995, pp. 871–874.

Shigeori Takenaka, et al., Electrochemically Active DNA Probes: Detection of Target DNA Sequences at Femtomole Level . . . , Analytical Biochemistry 218, (1994) month available, pp. 436–443.

D. E. Smith, et al., Second Harmonic Alternating Current Polarography with a Revrsible Electrode Process, Analytical Chemistry, vol. 33, No. 4, Apr. 1961, pp. 482–485.

Philip D. Voegel, et al., Electrochemical detection with copper electrodes in liquid chromatography and capillary electrophoresis, Ameican Laboratory, Jan. 1996, pp. 39–45.

(List continued on next page.)

Primary Examiner—Robert Warden
Assistant Examiner—Alex Noguerola
Attorney, Agent, or Firm—Flehr Hohbach Test Albritton & Herbert LLP

[57] ABSTRACT

A microfabricated capillary electrophoresis chip which includes an integral thin film electrochemical detector for detecting molecules separated in the capillary.

18 Claims, 8 Drawing Sheets

OTHER PUBLICATIONS

Jonathan M. Slater, et al., On–chip Microband Array Electrochemical Detector for use in Capillary Electrophoresis, Analyst, Nov. 1994, vol. 119, pp. 2303–2307.

Andrew G. Ewing, et al., Electrochemical Detection in Microcolumn Separations, Analytical Chemistry, vol. 66, No. 9, May 1, 1994, pp. 527A–536A.

Xiaohua Huang, et al., On–Column Conductivity Detector for Capillary Zone Electrophoresis, Analytical Chemistry, vol. 59, No. 23, Dec. 1, 1987, pp. 2747–2749.

Xiaohua Huang, et al., End–Column Detection for Capillary Zone Electropheresis, Analytical Chemistry, vol. 63, No. 2, Jan. 15, 1991, pp. 189–192.

Mei–Cheng Chen, et al., An Electrochemical Cell for End–Column Amperometric Detection in Capillary Electrophoresis, Analytical Chemistry, vol. 67, No. 21, Nov. 1, 1995, pp. 4010–4014.

Thomas J. O'Shea, et al., Capillary electrophoresis with electrochemical detection employing an on–column Nafion joint, Journal of Chromatography, 593, (1992) month unavailable, pp. 309–312.

Adam T. Woolley, et al., Ultra–High–Speed DNA Sequencing Using Capillary Electrophoresis Chips, Anal. Chem. 1995 month unavailable, 67, pp. 3676–3680.

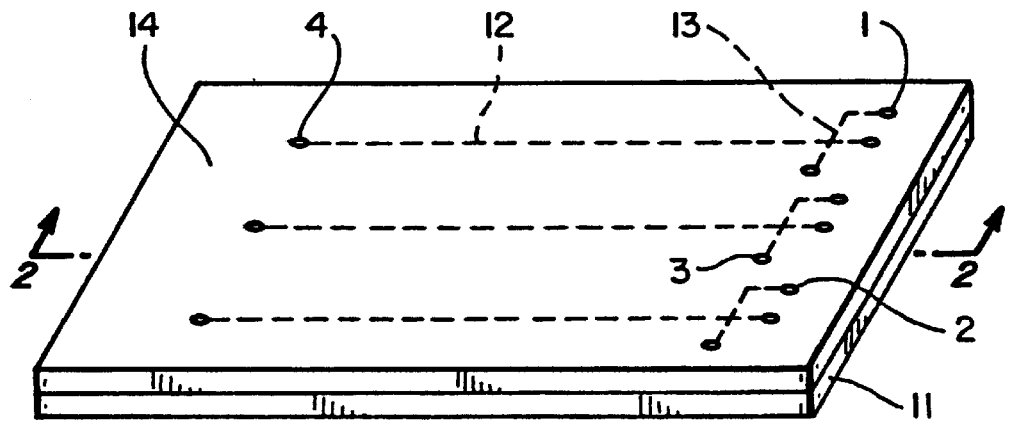
FIG_1
*(PRIOR ART)*
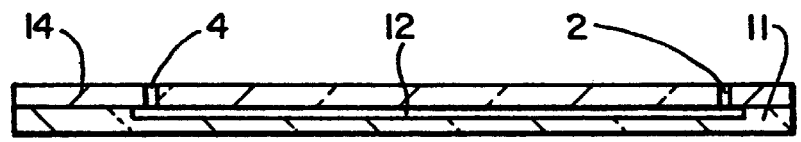
FIG_2
*(PRIOR ART)*
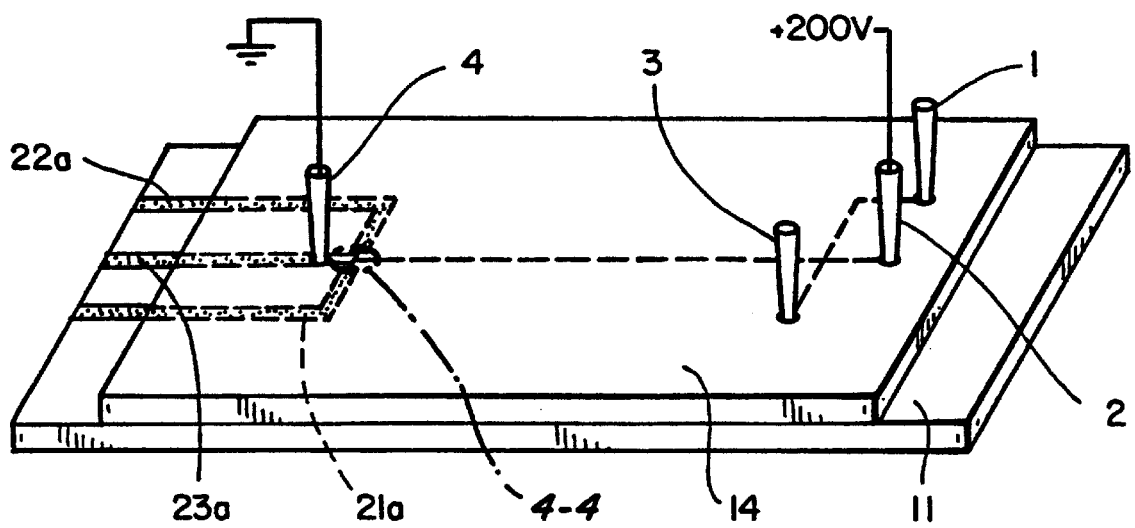
FIG_3

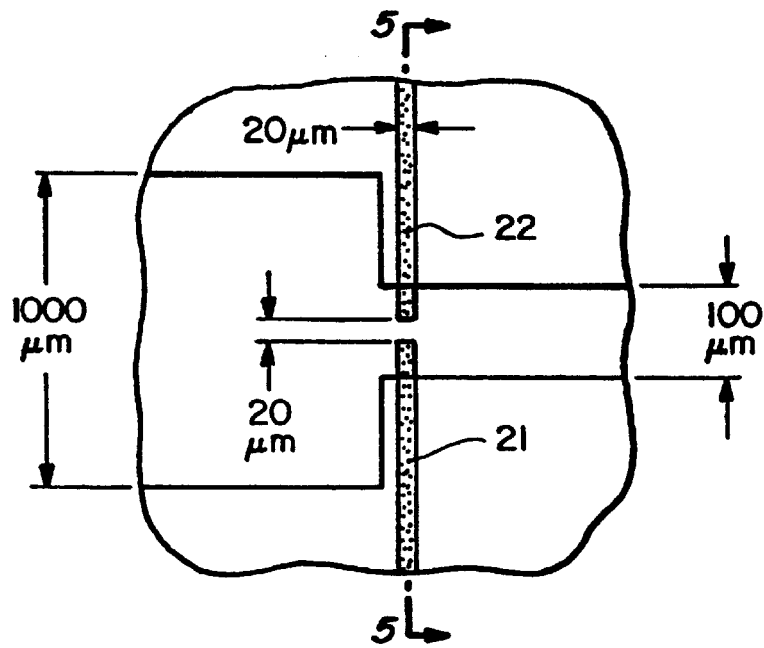
FIG_4
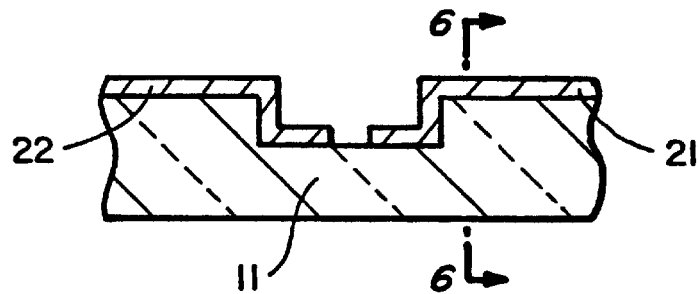
FIG_5
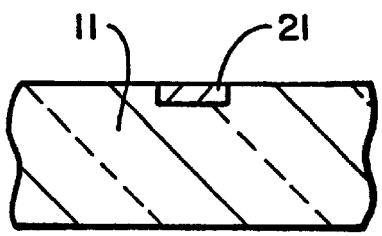
FIG_6

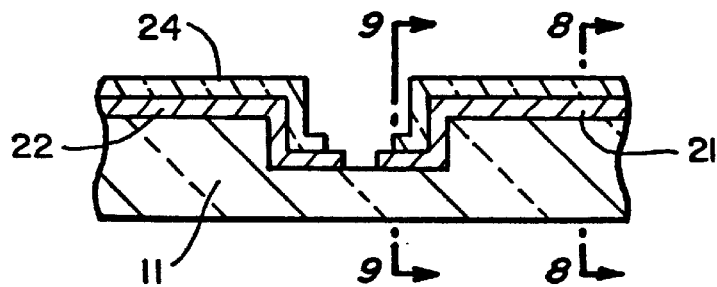
FIG_7
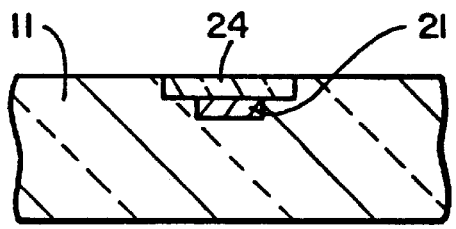
FIG_8
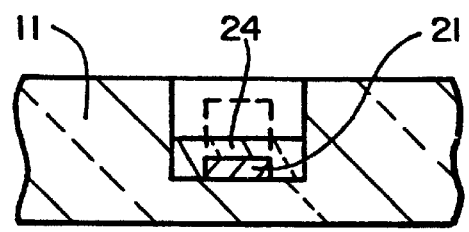
FIG_9
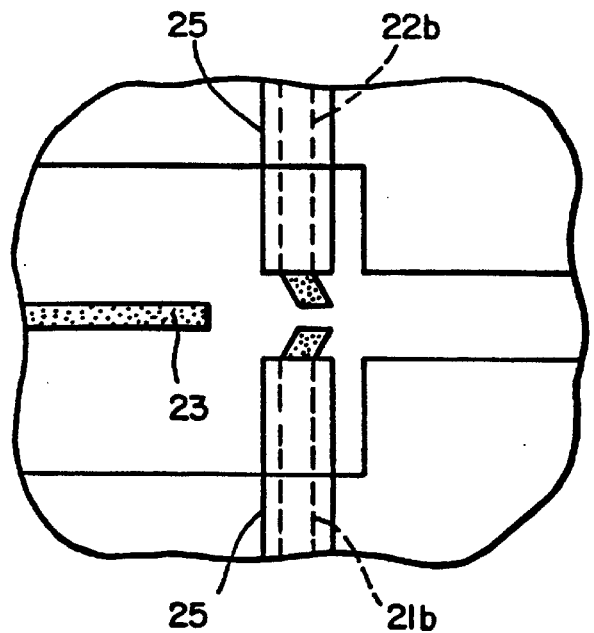
FIG_10

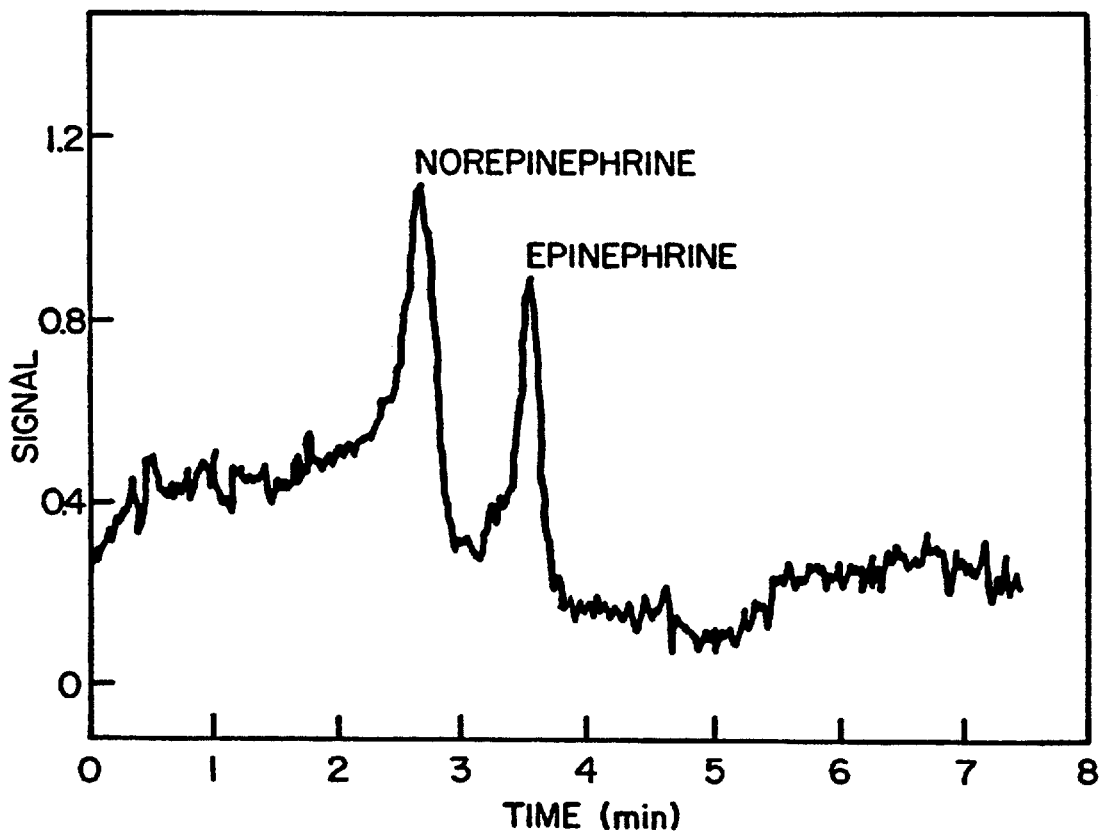
FIG_11
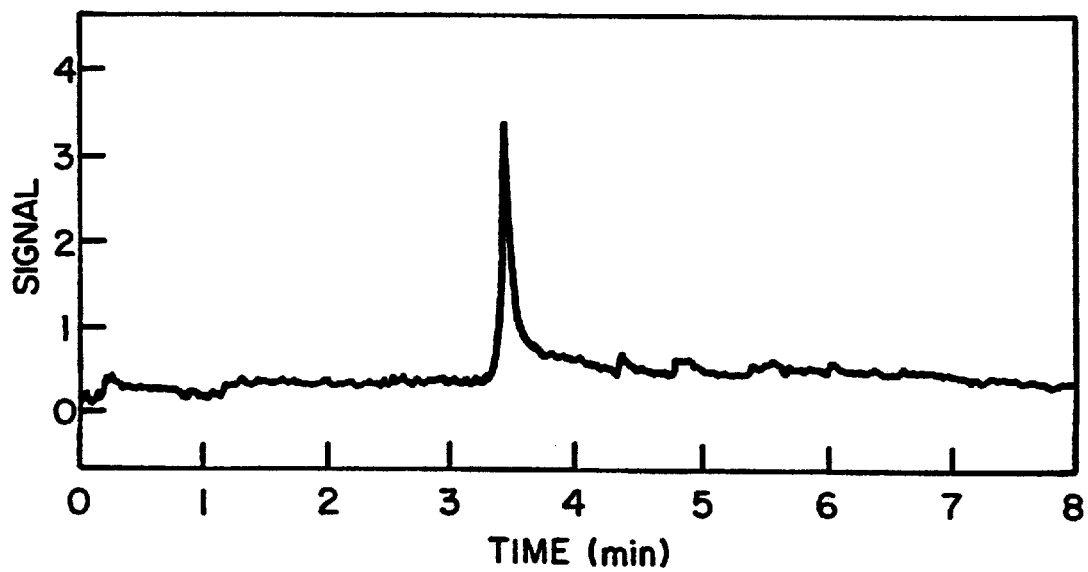
FIG_12A

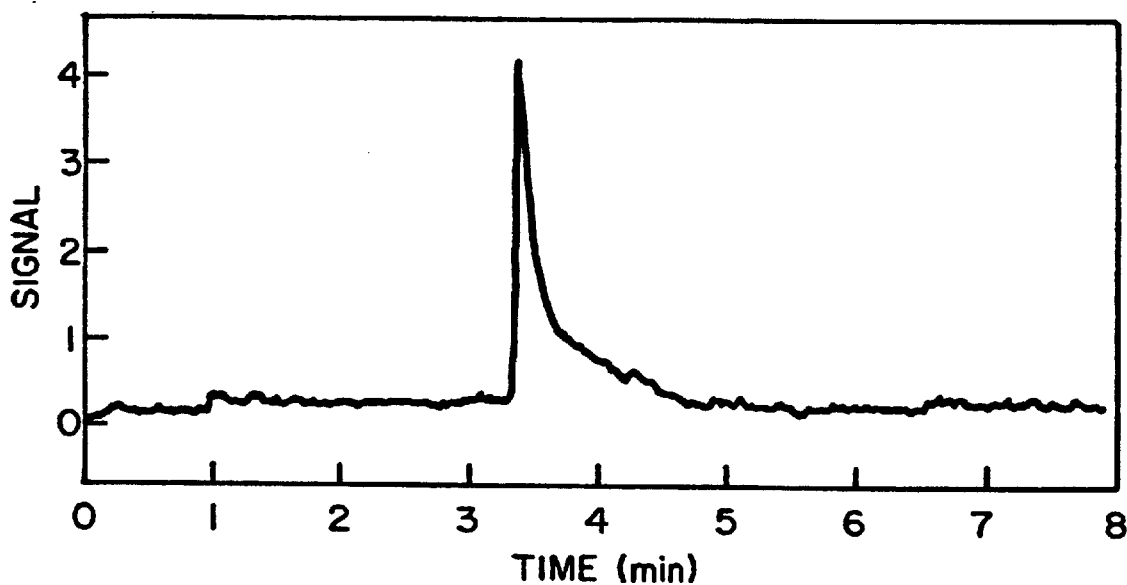
FIG_12B
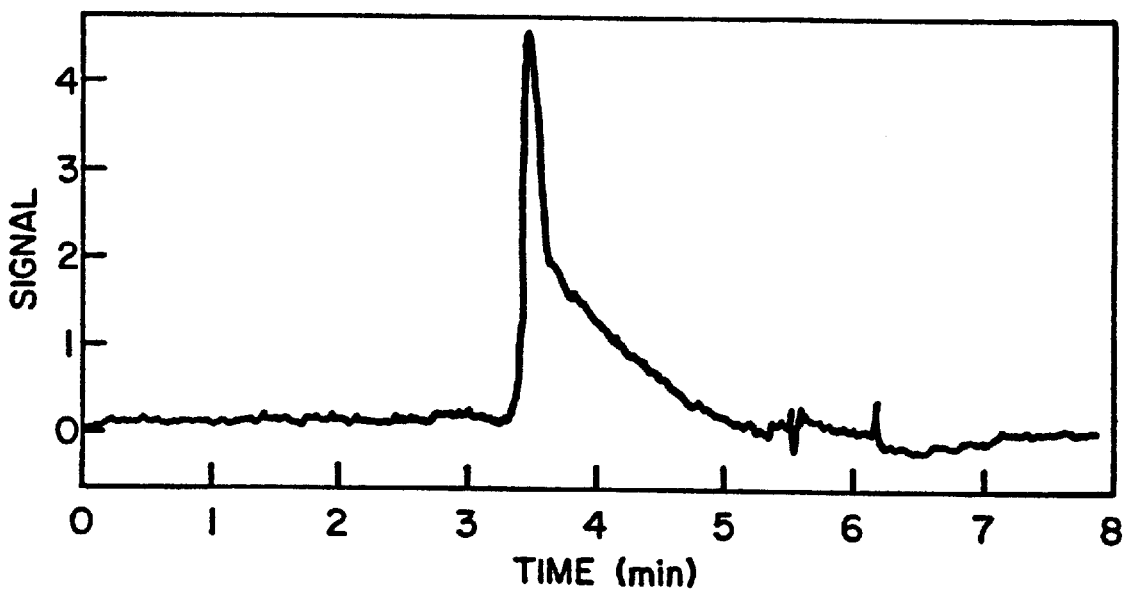
FIG_12C

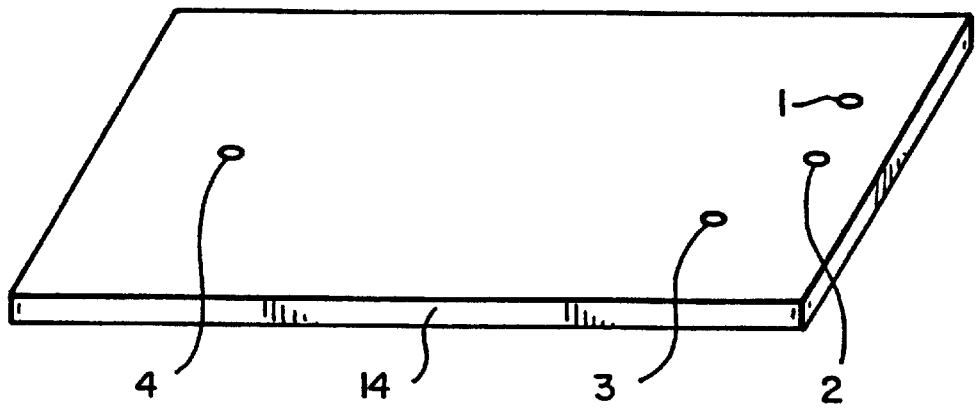
FIG_13A
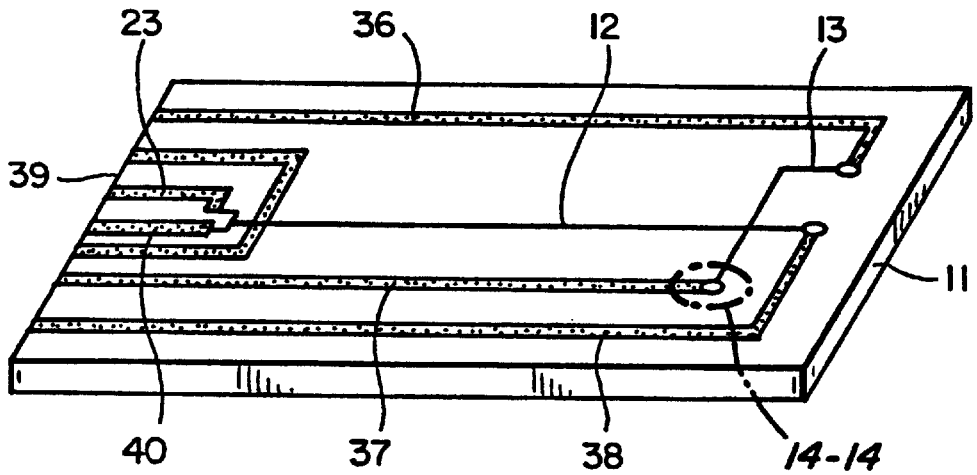
FIG_13B
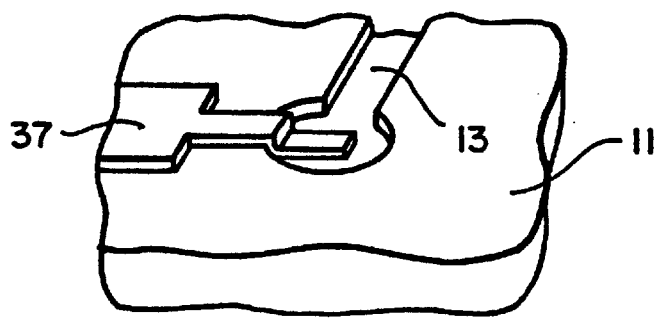
FIG_14

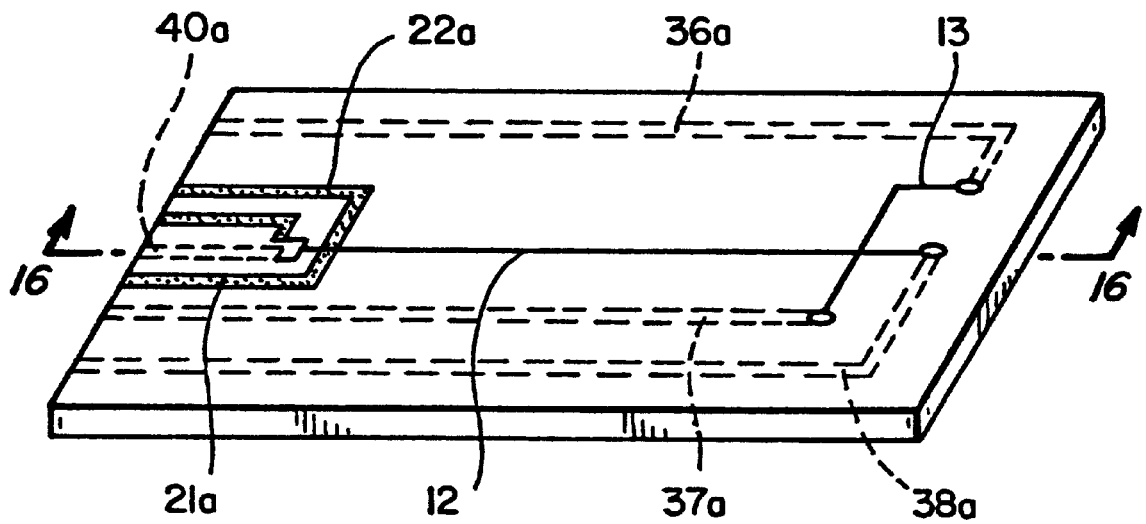
FIG_15
FIG_16
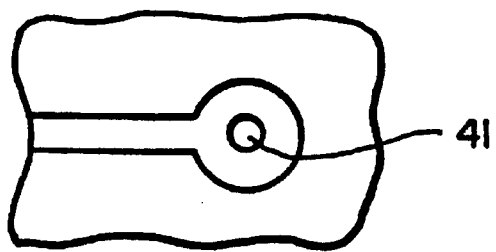
FIG_17

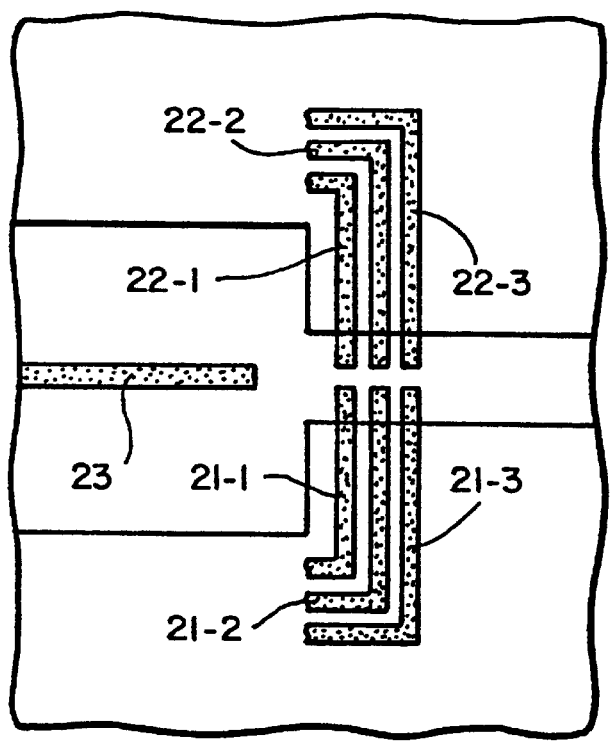
FIG_18
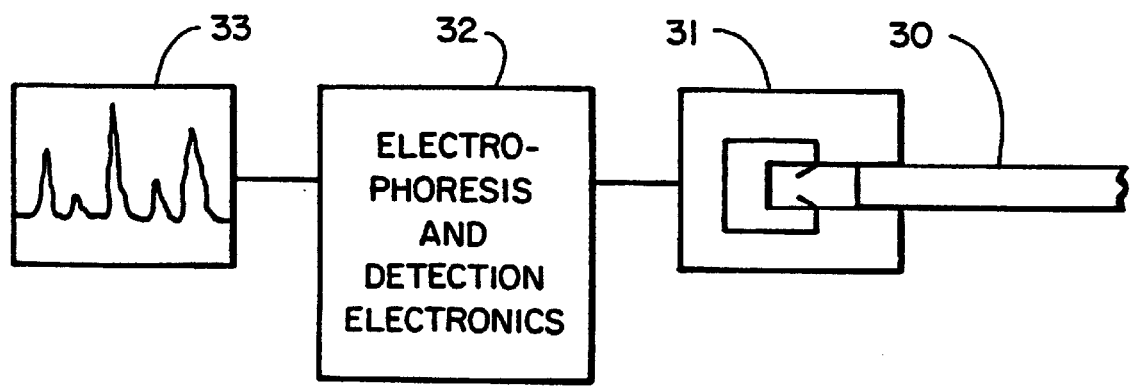
FIG_19

ELECTROCHEMICAL DETECTOR INTEGRATED ON MICROFABRICATED CAPILLARY ELECTROPHORESIS CHIPS

BRIEF DESCRIPTION OF THE INVENTION

This invention relates generally to an electrochemical detector as a component of an integrated separation and detection module on a microfabricated capillary electrophoresis chip and to a method of fabricating the electrochemical detector and more particularly to the design of a thin film electrochemical detector which can be precisely positioned in a microfabricated capillary.

BACKGROUND OF THE INVENTION

Electrochemical detection has been employed in liquid chromatography and in capillary electrophoresis (CE). It has been demonstrated that electrochemical detection is very sensitive and can measure $10^{-16}$ to $10^{-19}$ moles of sample with typical detection volumes from nL to pL[1,2]. Electrochemical methods have also been used to detect DNA,[3–5] single cells,[6,7] and even single molecules.[8] The operation of these electrochemical detectors is typically based on the use of three electrodes called the working, counter, and reference electrodes. There are three configurations which have been used to detect CE separations: on-column,[9] where the electrodes of the detector are placed within the capillary; end-column,[10,11] where the electrodes are placed directly at the end of the separation capillary; and off-column,[6,12,13] where the electrodes are electrically isolated from the electrophoresis voltage by a grounded porous glass tube. On-column electrochemical detection of CE separations has been performed by fixing two platinum wires through diametrically opposed holes drilled by a laser in a capillary tube. This structure is very difficult to manufacture and align, and the placement of the detection electrodes within the high voltage region of the separation column is problematic. In this format, one is trying to detect small currents or voltages while applying many kV to the separation column. The mechanical instability and poor definition of the electrode alignment can lead to significant electrical pickup or fluctuation in the background, making the desired signal very difficult to detect. The presence of high voltage gradients and significant electrophoretic currents in the column near the electrodes can induce stray signals. The end-column and off-column detection formats are important because they minimize the influence of the electrophoresis voltage. In the end-column format, one wants to place the detection electrodes as close to the end of the electrophoresis channel as possible so the detection is performed as close to ground potential as possible. This is very difficult to do with conventional manufacturing techniques. The electrodes must be placed with micron precision at the end of the capillary. Any error in the placement will cause loss of analyte signal if the electrodes are too far from the opening or high voltage pick up if the electrodes are placed within the separation column. Furthermore, fluctuations in electrode placement or electrode—electrode gap can cause severe fluctuations in the background signal producing noise. Typically, one must use micromanipulators and a microscope to assemble the detector. Furthermore, the engineering of the electrical isolation by connection of the separation and detection capillary tubes with a grounded porous glass tube in the off-column format is rather difficult to assemble and operate, and the junction can be mechanically unstable and poorly defined. In one case, although Slater and Watt (17) photolithographically fabricated electrodes on a substrate, because they did not make a fully integrated separation and detection device, they were forced to use said undesirable junctions to couple their detector to a conventional cylindrical capillary.

There is a need for a microfabricated capillary electrophoresis chip with integral thin film electrochemical detector and electrophoresis leads which can be easily connected to associated electrical electrophoresis and detector apparatus.

OBJECTS AND SUMMARY OF THE INVENTION

It is a general object of the present invention to provide an electrochemical detector for capillary electrophoresis on a microfabricated planar glass chip that overcomes the aforementioned short comings of the prior art.

It is another object of the present invention to provide a microfabricated capillary electrophoresis chip with a microelectrochemical detector that minimizes the effect of interference from applied electrophoresis fields.

It is another object of the present invention to provide detector electrodes which are reproducibly, accurately and conveniently placed, robust and sensitive.

It is a further object of the present invention to provide detector electrodes which are precisely and stably positioned at the very end of the capillary where they are close to ground potential and thereby immune to pick up from the high electrophoresis potentials.

It is a further object of the present invention to provide a microfabricated capillary electrophoresis chip with integrated thin film electrochemical detector electrodes and electrophoresis electrodes which can be produced accurately and at low cost.

The foregoing and other objects of the invention are achieved by integrating an electrochemical detector on a microfabricated capillary electrophoresis chip of the type including a substrate having at least an elongated separation channel and a cover plate bonded to said substrate to form with said channel a separation capillary. A thin film electrochemical detector is fabricated on the surface of said substrate or cover plate with thin narrow electrodes extending into said channel near one end of said channel.

BRIEF DESCRIPTION OF THE DRAWINGS

The foregoing and other objects of the present invention will be more clearly understood from the following description when read in conjunction with the accompanying drawings, of which:

FIG. 1 shows a microfabricated capillary electrophoresis chip in accordance with the prior art;

FIG. 2 is a sectional view taken along the line 2—2 of FIG. 1;

FIG. 3 is a perspective view of a microfabricated capillary electrophoresis chip incorporating the present invention;

FIG. 4 is an enlarged view of the indicated detector region 4—4 of FIG. 3;

FIG. 5 is a sectional view taken along the line 5—5 of FIG. 4;

FIG. 6 is a sectional view taken along the line 6—6 of FIG. 5;

FIG. 7 is a sectional view showing another embodiment of the electrochemical electrodes shown in FIGS. 3 and 4;

FIG. 8 is a sectional view taken along the line 8—8 of FIG. 7;

FIG. 9 is a sectional view taken along the line 9—9 of FIG. 7;

FIG. 10 is an enlarged view of another detector embodiment;

FIG. 11 is an electropherogram of norepinephrine and epinephrine separated on a capillary electrophoresis chip with integrated electrochemical detection;

FIGS. 12A–12C are electropherograms of norepinephrine separations obtained with a capillary electrophoresis chip with integrated electrochemical detection for three consecutive experiments;

FIGS. 13A–13B are perspective views of a microfabricated capillary electrophoresis chip with integrated electrochemical detection including thin film connections to the separation and injection channels;

FIG. 14 is an enlarged view of the section 14—14 of FIG. 13B;

FIG. 15 is a perspective view of a substrate including an integrated electrochemical detector and leads connected to the injection and separation channels;

FIG. 16 is a sectional view taken along the lines 16—16 of FIG. 15;

FIG. 17 is an enlarged view taken along the direction of arrow 17 of FIG. 16;

FIG. 18 is a partial enlarged view showing a plurality of electrochemical detection electrodes formed along the separation channel;

FIG. 19 is a block diagram of an apparatus for joining a capillary electrophoresis chip into an overall electrochemical separation and analysis system in accordance with the present invention.

DESCRIPTION OF PREFERRED EMBODIMENTS

FIGS. 1 and 2 show a microfabricated capillary electrophoresis (CE) chip formed in accordance with the prior art. The capillary channels are formed on an etched glass substrate 11 by photolithography and chemical etching. The process is described by Woolley et al., Ultra-High-Speed DNA Fragment Separations Using Microfabricated Capillary Array Electrophoresis Chips, Proc. Nat'l. Acad. Sci., USA, 91, 11348–11352 (1994)[14]. The separation channel 12 and the injection channel 13 for injecting sample into the channel by stack or plug injection are described in the above reference. In one example, all channels were etched to a depth of 8 $\mu$m; the separation channels were 100 $\mu$m wide, and the injection channels were 50 $\mu$m wide. The separation channels were 46 mm long, with a distance of 39 mm from the point of injection to the electrochemical detector. The injection channels were 22 mm long with a distance of 12 mm from the point of sample introduction to the injection region. A top plate 14 was bonded to the etched glass substrate to form the capillaries which are filled with a separation matrix. The top plate includes drilled holes 1–4 which provide reagent reservoirs to the ends of the separation channel and the ends of the injection channel.

In the prior art, the electrophoretic DNA separations in the microfabricated capillary channels were detected by bulky, inconvenient and costly systems employing external lasers, optical systems, photomultiplier tubes, etc. It has thus far not been possible to integrate the optical detection system onto a microfabricated CE chip. Similarly, although electrochemical detection of conventional capillary electrophoresis separations performed in hollow silica capillaries has been performed with a variety of external electrode and detector formats, such a detector has never been integrated within a CE electrophoresis chip system with a single microfabrication technology.

In accordance with one embodiment of the present invention, platinum electrodes for electrochemical detectors are fabricated on the substrate or top plate by RF by sputtering and photolithography before the top or cover plate is bonded to the etched substrate. The electrodes can be accurately positioned at the ends of the separation column where they are close to ground potential thereby providing a stable, easy to manufacture, inexpensive electrochemical detector. Other suitable electrode materials are gold, chromium, carbon and other relatively inert easily deposited conductive materials.

Referring to FIGS. 3–5, a CE chip is shown with thin film platinum electrodes. The electrodes comprise a reference electrode 21, a working electrode 22, and a counter electrode 23 (not shown) connected to an external circuit by thin film conductors 21a, 22a and 23a. The substrate is preferably etched so that the electrodes and thin film conductors are inset as shown in FIG. 6 whereby the top plate 14 can be effectively sealed to the substrate. The reference and working electrodes include a narrow portion extending into the channel with the ends separated and adapted to detect current or voltage as molecules undergo redox reactions or conduct current as they migrate past spaced electrodes. The electrodes are connected to wider thin film leads 21a, 22a and 23a which extend to the edge of the chip for insertion into a connector (not shown) to provide electrical connection to the electrical measuring circuits. In order to limit the exposed area of the narrow portions of the working and reference electrodes which extend into the channel, the electrodes can be covered with an insulating dielectric film such as $SiO_2$. This is illustrated in FIGS. 7–9 where the electrodes 21 and 22 are covered by an insulating film 24. In one example, the Pt electrodes were deposited using RF sputtering; the thickness of the electrodes was 3000 Å. The working and reference electrodes were 20 $\mu$m wide Pt electrodes that were precisely aligned on opposite sides of the channel (to minimize the potential difference between electrodes) and extended 40 $\mu$m into the channel, with a spacing of 20 $\mu$m (see FIG. 4). The 100 $\mu$m channel widens to 1000 $\mu$m at the end to increase the volume of separation channel. The working and reference electrodes were placed 20 $\mu$m from the point of widening. The counter electrode was 2 mm wide and extended into the widened portion at the end of channel. The advantage of this design is that it minimizes the influence of the electrophoresis voltage by working very close (20 $\mu$m) to the ground end of the channel where the analyte is still highly concentrated, while still performing on-column detection. After careful alignment, the etched bottom plate or substrate 11 with the Pt electrodes was thermally bonded to a top glass plate 14 with 0.8 mm holes 1–4. The detector electrodes can also be formed adjacent the end of the channel as shown in FIG. 10. The detector electrodes 21b and 22b are covered by an insulating film 25 with the ends exposed. Although specific dimensions have been given for the described embodiment, the channel width and depth can be between 1–500 $\mu$m, the electrode width 1–500 $\mu$m and the electrode spacing 1–500 $\mu$m.

The advantages of such fabrication and design are that (i) the working and reference electrodes can be easily and precisely positioned near, at, or just beyond the opening of the separation channel where pickup and interference from the electrophoresis voltage is minimal and where the analyte concentration in the separated zone is still high. This precise (micron) alignment is only possible with an integrated microfabricated device. (ii) The electrodes in the channel are very small in the electrophoresis dimension. This is advantageous because it facilitates the placement of multiple electrodes, FIG. 18, at essentially (compared to the zone size) the same point in the channel. It is also advantageous because we have observed that wider electrodes tend to nucleate electrolysis bubbles presumably because they sample more of the electrophoretic voltage gradient. This effect can be reduced by covering the body of the electrode (not the tip) with an insulating layer. Such thin electrodes can only be produced via photolithography on an integrated device. Finally, one wants to have a precise and small electrode gap so that each detector functions the same and has a similar sensitivity and probed volume. The ability to fabricate a small gap will produce low backgrounds because the effective volume of conductive and capacitive solution between the electrode is small. The ability to make detectors with small gaps is also advantageous because it permits the fabrication and detection of narrow separation channels which require only small amounts of sample and which have very high electrophoretic resolution.

It is noted that the channel widens at the end just past or at the point of detection. This is important because it keeps the first zones in the separation from raising the background as a result of diffusion of analyte back into the detector zone. By having a larger channel beyond the detector to provide a greater volume, the early zones are effectively diluted by the large solution volume around the counter electrode thereby keeping them from raising the background for the detection of subsequent bands. The wide section also has a low resistance because of its large cross section. This means that the voltage drop from the detector to the counter electrode will be much smaller thereby further reducing stray voltages at the detector and pickup and background. It will be appreciated that in addition to widening the channel to provide a greater volume, the depth may be increased.

Capillary zone electrophoresis separation of two neurotransmitters, epinephrine and norepinephrine was performed using a CE microchip having the dimensions given in the above examples following in general the methods outlined in Woolley et al[14–15]. A 30 mM solution of 2-(N-morpholino) ethanesulfonic acid (MES) adjusted to pH 5.6 with NaOH and modified with 20% (v/v) 2-propanol was used as the buffer. Stock solutions (10 $\mu$m) of epinephrine and norepinephrine (Sigma, St. Louis) were prepared in 0.01 M perchloric acid. Samples were serially diluted to the desired concentration in MES buffer. After placing the sample in reservoir 3, the samples were injected by applying 90 V/cm between reservoirs 1 and 3 (FIG. 3) for 20 seconds and the approximate injection volume was calculated as 40 pL. Separations were performed by applying 45 V/cm between reservoirs 2 and 4. The electrophoresis currents were typically 0.3 $\mu$A.

A Macintosh computer equipped with a National Instruments NB-MIO-16XL-18 I/O board was used to set voltages, store data and control the home-built three electrode potentiostat. The working electrode 22 was biased at +0.5 V relative to the reference electrode 21; the counter electrode 23 was used to complete the circuit. The potentiostat measured the current generated by molecules undergoing redox reactions as they migrated past the gap between the reference and working electrodes. Small currents (<1 pA) could be detected even in the presence of the larger DC electrophoresis current (0.3 $\mu$A) in the channels. Alternatively, the small currents could be detected by biasing the working electrode with an AC potential.[16] A lock-in amplifier could then be used to distinguish the signal from the DC electrophoresis current. Prior to experiments, the electrodes were cleaned using 1M $H_2SO_4$ with a sine wave potential ($V_{p-p}$=0.5V) applied to the electrodes for 20 minutes.

FIG. 11 shows the separation of two neurotransmitters, epinephrine and norepinephrine, performed on the microfabricated CE chip with integrated electrochemical detection. Norepinephrine and epinephrine were detected at 2.6 min and 3.4 min, respectively, and the peaks were baseline resolved. The separation time was short, approximately 3 minutes.

FIGS. 12A–12C present the injection and detection of 0.48 nM epinephrine in three consecutive times. The reproducibility of migration times for these runs is excellent. The reproducibility of the signal strength is within a factor of 1.5, and most of the variability can be attributed to tailing from the later injections.

In addition to the use of thin film detection electrodes, thin film connections can be made from the edge of the chip to the ends of the separation and injection channels, 12 and 13. This would then permit insertion of the chip 30 into the socket 31, (FIG. 19,) which provides electrical connection to electrophoresis and detection electronics 32, for example, a processor of the type described above. The processor can be used to control stack or plug injection of sample into the separation channel and to apply electrophoresis voltages to the separation channel. Furthermore, the processor can apply voltages to the detector and analyze redox currents to provide a display or printout 33.

Referring to FIGS. 13 and 14, thin film leads 36, 37, and 38 are shown connected to the ends of the injection channel and to one end of the separation channel or column. A thin film connection 40 to the other end of the channel is also shown. The thin film leads terminate at the edge 39 of the substrate. The thin film leads are carefully placed in all the reservoirs so that they are far from the end of the channels so that hydrolysis bubbles due to current flow at the lead do not enter the adjacent channel. This is illustrated in FIG. 14 for one end of the injection channel. The chip can then be inserted into the socket for carrying out sample analysis. After the thin film leads are formed by photolithography and sputtering, the cover 14 is bonded to the substrate spaced from the end so that the leads can be contacted.

In another example, thin film leads 36a, 37a, 38a and 40a can be formed at the bottom of the substrate, FIGS. 15–17 with lead through connections 39 to the bottom of the etched channels and spaced from the ends of the channel.

Discrimination between species with different half-cell potentials can be achieved by sweeping over different bias voltages at the working electrode or by using multiple pairs of working and reference electrodes 21-1, 21-2 and 21-3, and 22-1, 22-2 and 22-3 as shown in FIG. 18.

It should be apparent that the various thin film detector electrodes and thin film connections to the injection and separation channel can alternatively be made on the top cover plate which is then accurately positioned with respect to the channels.

Thus, there has been provided an improved integrated electrochemical detector on a microfabricated CE chip. This opens the way to a variety of interesting and useful analytes. For example, electrochemical detection on CE chips could be used for numerous analytes which are redox active. A microfabricated chip and electrochemical detector can be used for remote analysis of hazardous substances without the need for operator intervention. This invention is an important step towards complete integration of DNA and other analyses on microfabricated chips.

REFERENCES

1. Ewing, A. G.; Mesaros, J. M.; Gavin, P. F., Electrochemical Detection in Microcolumn Separations, Anal. Chem., 66, 527A–536A, (1994).

2. Voegel, P. D.; Baldwin, R. P., Electrochemical Detection with Copper Electrodes in Liquid Chromatography and Capillary Electrophoresis, American Laboratory, 28(2), 39–45, (1996).

3. Shigenaga, M. K.; Park, J.-W.; Cundy, K. C.; Gimeno, C. J.; Ames, B. N., In Vivo Oxidative DNA Damage: Measurement of 8-hydroxy-2'-deoxyguanosine in DNA and Urine by High-Performance Liquid Chromatography with Electrochemical Detection, Methods in Enzymol., 186, 521–530, (1990).

4. Takenaka, S.; Uto, H.; Knodo, H.; Ihara, T.; Takagi, M., Electrochemically Active DNA Probes-Detection of Target DNA Sequences at Femtomole Level by High-Performance Liquid Chromatography with Electrochemical Detection, Anal. Biochem., 218, 436–443, (1994).

5. Johnston, D. H.; Glasglow, D. C.; Thorp, H. H., Electrochemical Measurement of the Solvent Accessibility of Nucleobases Using Electron Transfer Between DNA and Metal Complexes, J. Am. Chem. Soc., 117 8933–8938, (1995).

6. Olefirowicz, T. M.; Ewing, A. G., Capillary Electrophoresis in 2 and 5 $\mu$M Diameter Capillaries: Application to Cytoplasmic Analysis, Anal. Chem., 62, 1872–1876, (1990).

7. Pihel, K.; Hsieh, S.; Jorgenson, J. W.; Wightman, R. M., Electrochemical Detection of Histamine and 5-Hydroxytryptamine at Isolated Mast Cells, Anal. Chem., 67, 4514–4521, (1995).

8. Fan, F.-R. F.; Bard, A. J., Electrochemical Detection of Single Molecules, Science, 267, 871–874, (1995).

9. Huang, X.; Pang, T.-K. J.; Gordon, M. J.; Zare, R. N., On-Column Conductivity Detector for Capillary Zone Electrophoresis, Anal. Chem., 59, 2747–2749, (1987).

10. Huang, X.; Zare, R. N.; Sloss, S.; Ewing, A. G., End-Column Detection for Capillary Zone Electrophoresis, Anal. Chem., 63, 189–192, (1991).

11. Chen, M.-C.; Huang, H.-J., An Electrochemical Cell for End-Column Amperometric Detection in Capillary Electrophoresis, Anal. Chem., 67, 4010–4014, (1995).

12. O'Shea, T. J.; Greenhagen, R. D.; Lunte, S. M.; Lunte, C. E.; Smyth, M. R.; Radzik, D. M.; Watanabe, N., Capillary Electrophoresis with Electrochemical Detection Employing an On-Column Nafion Joint, J. Chromatogr., 593, 305–312, (1992).

13. Wu, D.; Regnier, F. E.; Linhares, M. C., Electrophoretically Mediated Micro-Assay of Alkaline Phosphatase using Electrochemical and Spectrophotometric Detection in Capillary Electrophoresis, J. Chromatogr. B, 657, 357–363, (1994).

14. Woolley, A. T.; Mathies, R. A., Ultra-High-Speed DNA Fragment Separations Using Microfabricated Capillary Array Electrophoresis Chips, Proc. Nat'l. Acad. Sci., USA, 91, 11348–11352, (1994).

15. Woolley, A. T.; Mathies, R. A., Ultra-High-Speed DNA Sequencing Using Capillary Electrophoresis Chips, Anal. Chem., 67, 3676–3680, (1995).

16. Smith, D. E.; Reinmuth, W. H., Second Harmonic Alternating Current Polarography with a Reversible Electrode Process, Anal. Chem., 33, 482–485, (1961).

17. Slater, J. M.; Watt, E. J., On-chip Microbond Array Electrochemical Detector for use in Capillary Electrophoresis Analyst, 1994, 119, 2303–2307.

What is claimed is:

1. In a microfabricated capillary electrophoresis chip including a substrate with an elongated separation channel with conductive means at each end of the channel for applying a separation voltage along the channel, the improvement comprising an integrated electrochemical detector having a thin film working electrode extending into said separation channel at or near the very end of said separation channel where the working electrode is close to ground potential and has minimal influence from the high electrophoresis potentials, in order to detect current generated by molecules undergoing redox reaction as they migrate past the thin film electrode after they have migrated the length of the channel, the portion of said thin film electrode extending into said channel being very narrow to minimize the electrophoresis voltage gradient which it senses, and a reference electrode spaced from said working electrode.

2. A microfabricated capillary electrophoresis chip as in claim 1 in which the reference electrode is a narrow thin film electrode which extends into said channel towards and spaced from side working electrode to form a detection region therebetween within the electrophoresis channel or at or just beyond the end thereof.

3. A microfabricated capillary electrophoresis chip as in claim 2 in which said channel is from 1–500 $\mu$m wide, said narrow ends are from 1–500 $\mu$m wide and the spacing between the narrow ends is from 1–500 $\mu$m.

4. A microfabricated capillary electrophoresis chip as in claim 2 including thin film leads extending from said thin film working electrode and said conductive means at each end of the separation channel to the same edge of said chip.

5. A microfabricated capillary electrophoresis chip as in claim 1 in which said thin film working electrode is covered with an insulating film which extends to a point near the end of the electrode.

6. A microfabricated capillary electrophoresis chip as in claim 1 in which the channel at one end transitions to a larger volume portion and said thin film working electrode is placed in or near the transition to a larger volume.

7. A microfabricated capillary electrophoresis chip as in claim 1 including a plurality of pairs of spaced working electrodes disposed along said end of said channel to perform multiple electrochemical detection.

8. A microfabricated capillary electrophoresis chip including a substrate with an elongated separation channel and a cover plate mounted on said substrate to form, with said channel, a separation capillary comprising:

thin film conductive means at each end of said capillary for applying a separation voltage along said capillary, and an electrochemical detector having a thin film working electrode near the very end of said channel where the working electrode is close to ground potential and has minimal influence from the high electrophoresis potentials, wherein the thin film working electrode is adapted to detect molecules undergoing redox reaction as they migrate past the thin film electrode, the portion of said thin film working electrode extending into said channel being narrow and near the end of said capillary to minimize the separation voltage gradient which is senses, and a reference electrode spaced from said working electrode.

9. A microfabricated capillary electrophoresis chip as in claim 8 in which the thin film reference electrode extends into said channel towards and spaced from said working electrode to form a detection region therebetween within the capillary.

10. A microfabricated capillary electrophoresis chip as in claim 8 in which said thin film working electrode is covered with an insulating film which extends to a point near the end of the electrode.

11. A microfabricated capillary electrophoresis chip as in claim 8 in which said channel is from 1–500 μm wide, said narrow ends are 1–500 μm wide and the spacing between the ends is from 1–500 μm.

12. A microfabricated capillary electrophoresis chip as in claim 8 in which the channel transitions to a larger volume channel portion and said thin film working electrode is placed less than 500 μm from the transition to a larger volume.

13. A microfabricated capillary electrophoresis chip as in claim 8 including a plurality of pairs of spaced working electrodes disposed along said end of said capillary to perform multiple electrochemical detection.

14. A microfabricated capillary electrophoresis chip as in claim 8 including thin film leads extending from said thin film working electrode and said conductive means to one edge of said chip.

15. A microfabricated capillary electrophoresis chip including an etched glass substrate with an elongated separation channel and an injection channel and a cover plate mounted on said substrate to form, with said channels a separation and injection capillary comprising:

thin film leads extending from the same edge of said chip to connect to the ends of the separation and injection channels, an integrated electrochemical detector having a thin film working electrode extending from said one edge into said separation channel at or near the very end of said channel where the working electrode is close to ground potential and has minimal influence from the high electrophoresis potentials, in order to detect current generated by molecules undergoing redox reaction as they migrate past the thin film electrode after they have migrated the length of the channels, the portion of said thin film electrode extending into said channel being narrow to minimize the electrophoresis voltage gradient which it senses, and a reference electrode spaced from said working electrode.

16. A microfabricated capillary electrophoresis chip as in claim 15 in which the reference electrode is a thin film electrode extending from said one edge with a narrow end extending into said channel towards and spaced from said working electrode to form a detection region therebetween.

17. A microfabricated capillary electrophoresis chip as in claim 16 in which said channel is from 1–500 μm wide, said narrow ends are from 1–500 μm wide and the spacing between the ends is from 1–500 μm.

18. A microfabricated capillary electrophoresis chip as in claim 15 in which the channel transitions to a wider channel portion and said thin film electrodes are closely spaced from said channel transition.

* * * * *

UNITED STATES PATENT AND TRADEMARK OFFICE
CERTIFICATE OF CORRECTION

PATENT NO. : 5,906,723                                       Page 1 of 2
DATED : May 25, 1999
INVENTOR(S) : Mathies et al.

It is certified that error appears in the above-indentified patent and that said Letters Patent is hereby corrected as shown below:

On the title page:

Pages 1-2, item [56], "OTHER PUBLICATIONS":
Page 1, first two lines, change "Electrochenical" to -- Electrochemical--;

column 2, line 3, change "month unavailable" to --July--;
column 2, line 7, change "656 (1994) month unavailable" to --567 (1994) July 15--;
column 2, line 12, change "month unavailable" to --September 6--;
column 2, line 15, change "month unavailable" to --September 1--;
column 2, line 19, change "month unavailable" to --December 15--;
column 2, lines 24-25, change "month unavailable" to --May 1--;
column 2, line 31, change "Ameican" to --American--.

Page 2, column 2, lines 8-9, change "month unavailable, pp. 309" to --February 28, pp. 305--;

column 2, line 12, change "month unavailable" to -- October 15 --.

Col. 4, line 3, delete "by". (2nd occurrence).

Col. 6, line 9, change "nM" to --$\mu$M--.

UNITED STATES PATENT AND TRADEMARK OFFICE
CERTIFICATE OF CORRECTION

PATENT NO. : 5,906,723
DATED : May 25, 1999
INVENTOR(S) : Mathies et al.

It is certified that error appears in the above-identified patent and that said Letters Patent is hereby corrected as shown below:

Col. 7, line 64, insert a comma (,) before "Analyst"

Signed and Sealed this

Twenty-eighth Day of December, 1999

Attest:

Q. TODD DICKINSON

Attesting Officer    Acting Commissioner of Patents and Trademarks